United States Patent
Herrera Sanchez et al.

(10) Patent No.: US 9,034,335 B2
(45) Date of Patent: May 19, 2015

(54) ADULT STEM CELL DERIVED CONDITIONED MEDIUM AND/OR ADULT STEM CELLS FOR USE IN THE THERAPEUTIC TREATMENT OF A TUMOR DISEASE

(75) Inventors: Maria Beatriz Herrera Sanchez, Turin (IT); Valentina Fonsato, Pecetto Torinese (IT); Ciro Tetta, Mirandola (IT); Giovanni Camussi, Turin (IT)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 4 days.

(21) Appl. No.: 13/514,719

(22) PCT Filed: Dec. 7, 2010

(86) PCT No.: PCT/EP2010/069049
§ 371 (c)(1),
(2), (4) Date: Jun. 8, 2012

(87) PCT Pub. No.: WO2011/070001
PCT Pub. Date: Jun. 16, 2011

(65) Prior Publication Data
US 2012/0251489 A1    Oct. 4, 2012

(30) Foreign Application Priority Data
Dec. 9, 2009  (EP) .................................... 09425504

(51) Int. Cl.
*A61K 39/00*   (2006.01)
*A61K 35/12*   (2006.01)
*C12N 5/071*   (2010.01)
*A61K 35/28*   (2006.01)

(52) U.S. Cl.
CPC .............. *C12N 5/0672* (2013.01); *A61K 35/28* (2013.01); *A61K 35/35* (2013.01); *C12N 2500/84* (2013.01); *C12N 2501/11* (2013.01); *C12N 2501/39* (2013.01); *C12N 2502/14* (2013.01)

(58) Field of Classification Search
None
See application file for complete search history.

(56) References Cited

U.S. PATENT DOCUMENTS 7,993,918 B2 *   8/2011   Paludan et al. ................ 435/375

FOREIGN PATENT DOCUMENTS

| WO | WO 2005/068612 A2 | 7/2005 |
|---|---|---|
| WO | WO 2006/126219 A1 | 11/2006 |
| WO | WO 2006/126236 A1 | 11/2006 |
| WO | WO 2008/020815 A1 | 2/2008 |
| WO | WO 2009-105044 A1 | 8/2009 |
| WO | WO 2009/150199 A1 | 12/2009 |

OTHER PUBLICATIONS

Suzuki et al. J. of Neuro-Oncology, 2005, v.74 pp. 233-239.*
F. Franhi et al. "Elevated doses of carmustine and mitcmycin C, with lonidamine enhancement and autologous bone marrow transplantation in the treatment of advanced colorectal cancer: Results from a pilot study" European Journal of Cancer, vol. 30, No. 10, Jan. 1, 1994, pp. 1420-1423.
P. Mulder et al. "High-dose chemotherapy with autologous bone marrow transplantation in patients with refractory ovarian cancer" European Journal of Cancer and Clinical Oncology, vol. 25, No. 4, Apr. 1, 1989. pp. 645-649.
K. Pardali et al. "Actions of TGF-beta as tumor suppressorand prometastatic factor in human cancer" Biochimica et Biophysics Acta, vol. 1775, No. 1, Jan. 1, 2007, pp. 21-62.
A. Cucina et al. "Zebrafish embryo proteins induce apoptosis in human colon cancer cells (Caeo2)" Apoptosis, (2006) 11:1617-1628.
L. Lee et al. "The fate of human malignant melanoma cells transplanted into zebrafish embyros: assessment of migration of cell division in the absence of tumor formation" Developmental Dynamics, 223: 1560-1570, 2005.
L. Postovit et al. "Human embryonic stem cell microenvironment suppresses the tumorigenic phenotype of aggressive cancer cells" PNAS, bo. 105, No. 11, Mar. 18, 2008, pp. 4329-4334.
D. Giuffrida et al. "Human embryonic stem cells secrete soluble factors that inhibit cancer cell growth" Cell Prolif. 2009, 42, 788-798.

* cited by examiner

*Primary Examiner* — Michail Belyavskyi
(74) *Attorney, Agent, or Firm* — Jacobson Holman, PLLC.

(57) ABSTRACT

The invention is in the field of therapeutic treatment of tumors. It has been found that the conditioned medium resulting from culturing an adult stem cell capable of differentiating into a plurality of differentiated cell types in a liquid cell culture medium and/or the adult stem cell from which the conditioned medium is obtainable, exert a remarkable anti-tumor effect. The adult stem cell derived conditioned medium preferred in this therapeutic application is a cell free conditioned medium derived from a human liver stem cell (HLSC).

17 Claims, 6 Drawing Sheets

ADULT STEM CELL DERIVED CONDITIONED MEDIUM AND/OR ADULT STEM CELLS FOR USE IN THE THERAPEUTIC TREATMENT OF A TUMOR DISEASE

This is a national stage of PCT/EP10/069049 filed Dec. 7, 2010 and published in English, which claims the priority of European number 09425504.9 filed Dec. 9, 2009, hereby incorporated by reference.

The present invention relates to the field of therapeutic treatment of tumour diseases.

Metastatic cancer cells share many characteristics with stem cells such as their ability to self-renew and to generate a diverse progeny. Moreover, the phenotype of stem cells and cancer cells is profoundly influenced by the microenvironment. At the same time, the embryonic microenvironments have been shown to inhibit the tumorigenicity of a variety of cancer cell lines. It was demonstrated that exposure of metastatic melanoma cells to an embryonic zebrafish microenvironment, before gastrulation, results in their reprogramming toward a non-tumorigenic phenotype (Cucina A, et al. (2006). Zebrafish embryo proteins induce apoptosis in human colon cancer cells (Caco2). *Apoptosis* 11:1615-1628; Lee L M, et al. (2005). The fate of human malignant melanoma cells transplanted into zebrafish embryos: Assessment of migration and cell division in the absence of tumor formation. *Dev Dyn* 233:1560-1570). In addition, the metastatic melanoma cells transplanted into developing chick embryos are capable of following neural crest migration pathways, resulting in a loss of tumorigenicity and in the acquisition of a neural crest-like phenotype. Recent studies have shown that the human embryonic stem cells (hESC) microenvironment specifically neutralizes the expression of the embryonic morphogen Nodal in metastatic melanoma and breast carcinoma cells, reprogramming them to a less aggressive phenotype (Postovit L M et al. (2008). Human embryonic stem cell microenvironment suppresses the tumorigenic phenotype of aggressive cancer cells. *PNAS* 105: 4329-4334). Postovit L M et al. uncovered hESC-secreted Lefty, an inhibitor of Nodal signalling, as one of the important mediator of these phenomena. These studies demonstrated that the microenvironment of embryonic stem cells provides a previously unexplored therapeutic entity for the regulation of aberrantly expressed embryonic factors in aggressive tumour cells.

In Giuffrida D et al. Human embryonic stem cells secrete soluble factors that inhibit cancer cell growth. *Cell Prolif.* 2009 Sep. 1, it was shown that inhibition of the proliferation of human epithelial cancer cell lines is mediated by soluble factors produced by hESC. The authors found that the proportion of cancer cells in G(1) phase was increased by hESC CM treatment, accompanied by decrease in cells in S and G(2)/M phases, suggests that these factors slow down the progression of cancer cells by cell cycle inhibition.

However, such results have been achieved by embryonic stem cells that are difficult to obtain and give rise to both ethical and methodological concerns, in that destruction of the embryo is needed to obtain the embryonic stem cells. Furthermore, embryonic stem cells may undergo uncontrolled proliferation upon transplantation in vivo.

Human adult non-oval liver stem/progenitor cells (HLSCs) expressing both mesenchymal and embryonic stem cells markers and having multipotent differentiation abilities and regenerative properties were disclosed by the present inventors in the International patent application published as WO 2006/126219.

Although in WO2006126219 the HLSCs were defined as "pluripotent progenitor cells", it should be understood that the expressions "progenitor cells" and "stem cells" both refer to cells which are capable of self-renewing and differentiating into specialized (i.e. differentiated) cell types.

Furthermore, the terms "multipotent" and "pluripotent" are considered to be interchangeable within the context of the present description, in that they both refer to the ability of a stem/progenitor cell to differentiate into a plurality of specialized (differentiated) cell types. Within this context, the term "a plurality" means at least two, preferably at least three, specialized (differentiated) cell types.

Within the context of the present description, the expression "adult stem cell" is intended to mean a stem cell that is isolated from an adult tissue, in contrast with an "embryonic stem cell" which is isolated from the inner cell mass of a blastocyst. Adult stem cells are also known as "somatic stem cells".

The human non-oval liver pluripotent progenitor/stem cells disclosed in WO 2006/126236 were shown to undergo differentiation into a variety of tissue cell types (namely, mature liver cells, epithelial cells, insulin-producing cells and osteogenic cells) and to exert organ regenerating effects. Such cells are derived from a non-oval human liver pluripotent progenitor cell line which expresses hepatic cell markers. Such cells are isolated by a method comprising the steps of:
  (i) culturing adult liver-derived human mature hepatocytes in a cell culture medium until death of mature hepatocytes and selection of a population of surviving cells having epithelioid morphology;
  (ii) expanding the population of surviving cells having epithelioid morphology by culturing in a serum-containing, glucose-containing culture medium supplemented with hEGF (human epithelial growth factor) and bFGF (basic fibroblast growth factor) and comprising the usual inorganic salts, amino acids and vitamins necessary for the growth of mammalian cells and in particular wherein the mature hepatocytes are frozen in a serum-containing culture medium in the presence of a cryoprotecting agent and then thawed prior to culturing according to step (i).

The characterization of the human non-oval liver stem/progenitor cells disclosed in WO 2006/126236 and the method of preparing thereof are herein fully incorporated by reference.

It is also known in the art that preparations of mesenchymal stem cells (MSCs) exert a regenerative effect on some tissues. For example, bone marrow-derived MSCs are known to naturally support hematopoiesis by secreting a number of trophic molecules, including soluble extracellular matrix glycoproteins, cytokines and growth factors.

However, some stem cell preparations have the major disadvantage of causing immune reactions when administered. Some stem cell preparations even have the potential to cause cancer.

The present inventors have now found that the conditioned medium (CM) resulting from culturing, in a liquid cell culture medium, an adult stem cell which is sufficiently undifferentiated to be capable of giving rise to a plurality of differentiated cell types, unexpectedly shows an effective anti-tumour activity, as demonstrate by the in vitro and in vivo experimentations illustrated below in the experimental section of the description.

The conditioned medium (CM) suitable for use in the anti-tumour therapeutic application of the invention comprises a plurality of molecules and biomolecules, particularly proteins, more particularly cytokines, secreted by the stem cell during culturing.

Thus, a first aspect of the present invention is a conditioned medium which comprises a plurality of cell-secreted proteins and which is obtainable by culturing in a liquid cell culture medium an adult stem cell capable of differentiating into a plurality of differentiated cell types, for use in the therapeutic treatment of a tumour disease.

In a preferred embodiment, the conditioned medium is cell free. In another embodiment, the conditioned medium comprises a cell fraction consisting of the adult stem cell from which the conditioned medium is obtainable. Alternatively, the adult stem cell itself as defined above is used for the therapeutic treatment of a tumour disease.

Another aspect of the present invention is the use of the conditioned medium which comprises a plurality of cell-secreted proteins and which is obtainable by culturing in a liquid cell culture medium an adult stem cell capable of differentiating into a plurality of differentiated cell types, for preparing a medicament for the therapeutic treatment of a tumour disease. Either the cell free or the cell fraction-containing conditioned medium is suitable for use in the therapeutic treatment of a tumour disease. However, the cell free conditioned medium is preferred.

A cell free conditioned medium suitable for use in the treatment of a tumour disease according to the preferred embodiment of the invention is obtainable for example by a method comprising:
(i) culturing an adult stem cell capable of differentiating into a plurality of differentiated cell types in a liquid cell culture medium for a predetermined period of time, and
(ii) removing the cell fraction from the liquid cell culture medium, thereby obtaining a cell free conditioned medium which comprises a plurality of cell-secreted proteins.

A liquid cell culture medium suitable for obtaining the conditioned medium useful for the treatment of a tumor disease is disclosed in the experimental section of the patent description.

However, it is to be understood that any liquid cell culture medium suitable for culturing mammalian stem or progenitor cells, preferably human stem or progenitor cells, can be used to obtain the cell culture medium according to the present invention. The following alternative media are mentioned by way of non-limiting examples: Dulbecco's Modified Eagle Medium Nutrient Mixture F-12(DMEM/F-12), Roswell Park Memorial Institute medium (RPMI-1640), Minimum Essential Medium (MEM) Alpha Medium (α-MEM), Medium 199 and Iscove's Modified Dulbecco's Medium (IMDM)

The selection and the use of a suitable culture medium, which may depend e.g. on the particular type of stem cell used for producing the culture medium, is well within the knowledge and abilities of the person skilled in the art.

In a preferred embodiment, the cell fraction is cultured for a predetermined period of time, then it removed from the liquid cell culture medium by centrifugation or filtration. A suitable predetermined period of time is for example comprised between 6 to 48 hours, preferably between 12 to 24 hours. Any culture medium suitable for cultivation of adult stem/progenitor animal or human cells, preferably mammal cells, under non-differentiating conditions is suitable for use as the liquid cell culture medium.

After the removal of the cell fraction, the cell-free conditioned medium thereby obtained is optionally subjected to a further purification step e.g. by ultracentrifugation. Ultracentrifugation is conveniently carried out at about 20,000 to 300,000 g, preferably at about 80,000 to 200,000 g for about 1 hour at a temperature lower than room temperature, e.g. at about 4° C.

Further optional purification steps are the removal of the fraction of matter having a Nominal Molecular Weight (NMW) lower than about 3 KDa, which is effected e.g. by ultrafiltration, and/or the treatment with RNase in order to degrade any free RNA possibly contained within the conditioned medium.

Any stem cell/progenitor cell capable of differentiating into a plurality of differentiated cell types and isolated from and adult tissue, as opposed to an embryonic stem cell, is suitable for producing the conditioned medium useful in the therapeutic application of the invention. In a preferred embodiment, the adult stem cell is selected from the group consisting of a liver stem cell, a renal stem cell, an adipose stem cell, a mesenchymal stem cell, a perivascular multipotent progenitor cell, a dental pulp stem cell, an epithelial stem cell, a hematopoietic stem cell, a stem cell from exfoliated deciduous teeth and an umbilical cord stem cell. The adult stem cell can either be an animal stem cell or a human stem cell. Human stem cells are preferred when the therapeutic treatment is to be administered to a human patient.

In a preferred embodiment, the adult stem cell is a non-oval liver stem cell, preferably the non-oval human liver pluripotent progenitor cell (HLSC) disclosed in WO 2006/126236.

However, a conditioned medium effective for the therapeutic treatment of a tumor disease is also obtainable from other stem cells such as those mentioned in the preceding paragraph.

The "Comparative Example" provided in the experimental section of the patent description shows that both HLSC-CM and MSC-CM are effective in increasing apoptosis of the HepG2 cells, although HSLC-CM is more effective than MSC-CM. The comparative Example also shows that both conditioned media (HSLC-CM and MSC-CM) are more effective than TGF-β alone.

In the following, the conditioned medium derived from a non-oval liver stem cell, preferably the non-oval human liver pluripotent progenitor cell disclosed in WO 2006/126236, shall be referred to as the "HLSC-CM". HLSC-CM is preferably cell free.

In a preferred embodiment, the HLSCs have the features summarised in Table I, page 7 of WO2006/126236 (wherein said cells are designated as "HuHEP"), which illustrates their characterization by FACS and immunofluorescence analysis. The results of such analysis are reported herein below.

| Marker | |
|---|---|
| | FACS analysis (% of positive cells: mean ± SD) |
| CD34 | − |
| CD45 | − |
| CD14 | − |
| CD73 | + |
| CD29 | + |
| CD44 | + |
| CD117 (c-Kit) | − |
| CD90 (Thy-1) | + |
| CD146 | − |
| CD133 | − |
| CD105 (endoglin) | + |
| | Immunofluorescence analysis (% of positive cells: mean ± SD) |
| α-fetoprotein (AFP) | + |
| CK18 | + |

| Marker | |
|---|---|
| CK19 | − |
| Albumin(ALB) | + |
| HLA-A, B, C | + |

The composition of the HLSC-CM obtained from the non-oval human liver pluripotent progenitor cell disclosed in WO 2006/126236 has been characterized and disclosed in International patent application PCT/EP2009/057232. Such features are hereby incorporated by reference.

By way of example, the cell-free HLSC-CM is obtained by culturing the HLSCs disclosed in WO 2006/126236 either under GMP conditions, which are known to the skilled person, or in a BAL (BioArtificial Liver) system, which is also known to the skilled person.

An example of GMP conditions for growing liver pluripotent progenitor/stem cells and collecting the cell-free conditioned medium (CM) thereof is as follows.

Liver pluripotent progenitor/stem cells are isolated by the method disclosed in WO2006/126236, in which the expansion step is carried out by culturing the progenitor stem cells in the presence of foetal calf serum (FCS) preferably at a concentration of about 10%, hEGF (human epithelial growth factor) and bFGF (basic fibroblast growth factor). FCS, bFGF and hEGF are preferably GMP grade, e.g. those produced by Invitrogen.

For collecting the conditioned medium in GMP conditions, FCS is removed from the culture, since this is an heterologous protein that is not suitable for injection into humans. To that end, the cells are washed and cultured for 24 hours in a collecting medium comprised e.g. of alpha-MEM supplemented with GMP grade human albumin. Albumin is preferably at a concentration of about 0.05%. Alternatively, alpha-MEM alone or alpha-MEM supplemented with 2% FCS may be used. The cell-free conditioned medium is then collected by centrifugation or filtration.

According to one embodiment of the invention, the tumour disease is a solid tumour. Preferably, the tumour disease is selected from the group comprising liver tumour, epithelial tumour, breast tumour, lung tumour, prostate tumour, gastric tumour and colon tumour. More preferably, the tumour disease is hepatoma, Kaposi's sarcoma or breast adenocarcinoma.

The cell-free conditioned medium is either used as such or in a concentrated form. A concentrated form is concentrated for example at least approximately 5-fold, preferably at least approximately 10-fold, more preferably at least approximately 20-fold, even more preferably approximately 25-fold. The cell-free conditioned medium is administered either locally or systemically. A pharmaceutical dosage form suitable for both local and systemic administration is an injectable dosage form. By way of example, the cell-free CM can be administered by local intra-tumour (i.t.) injection when the tumour is a solid one, or by i.v. injection in the case of metastasis.

Further objects and advantages of the invention will appear more clearly from the following experimental section, which is provided purely by way of illustration. In the experimental section, reference is made to the following figures:

FIG. 1 is a graph showing the results of in vitro proliferation assays carried out by incubating HepG2 cells with different doses of 25× concentrated HLSC-CM for 48 hours. Proliferation of HepG2 was evaluated by BrdU incorporation assay after 48 hours of incubation. HepG2 were cultured in DMEM only or in DMEM supplemented with 0.5; 2; 8 or 16% of 25× concentrated CM. After 48 hours, the proliferation of HepG2 cells was quantified using BrdU incorporation assay. The experiments were performed in quadruplicate. The data shown are mean±standard deviation of eight experiments. P<0.05.

FIG. 2 is a graph showing the results of in vitro proliferation assays carried out by incubating HepG2 cells with different doses of 25× concentrated HLSC-CM for 4 days. Proliferation of HepG2 was evaluated by BrdU incorporation assay after 4 days of incubation. HepG2 were cultured in DMEM only or in DMEM supplemented with 1; 8 or 16% of 25× concentrated HLSC-CM for 4 days. The experiments were performed in quadruplicate. The data shown are mean±standard deviation of eight experiments. P<0.05.

FIG. 3 is a graph showing the results of in vitro proliferation assays carried out by incubating HepG2, MCF-7 and Kaposi cells (KS) with two different preparations of 25× concentrated HLSC-CM. Proliferation of HepG2, MCF-7 and Kaposi cells (KS) was evaluated by BrdU incorporation assay after 48 hours of incubation with 16% of 25× concentrated CM derived from HLSC6b and from HLSC2. The experiments were performed in duplicate. The data shown are mean±standard deviation of four experiments. P<0.05.

FIG. 4 is a graph showing the results of in vitro apoptosis assays carried out by incubating HepG2 cells with 25× concentrated HLSC-CM. Apoptosis of HepG2 was evaluated by TUNEL assay as the percentage of apoptotic cells after 24-hours of incubation with different doses of CM (0.5; 1; 2; 6; and 16% of 25× concentrated CM). Vincristine and Doxorubicin were used as the positive control of apoptosis induction; in the negative control HepG2 were treated with vehicle alone. The results are expressed as mean±SD of 3 different experiments.

FIG. 5 is a graph showing the results of in vitro apoptosis assays carried out by incubating HepG2, MCF-7 and KS cells with 25× concentrated HLSC-CM. Apoptosis of HepG2, MCF-7 and KS cells was evaluated by TUNEL assay as the percentage of apoptotic cells after 72-hours of incubation with 16% of 25× concentrated CM derived from two different cell preparation (HLSC-6B and HLSC-2). Vincristine was used as the positive control of apoptosis induction; in the negative control, the cells were treated with vehicle alone. The results are expressed as mean±SD of 3 different experiments. P<0.05.

Figure 9:
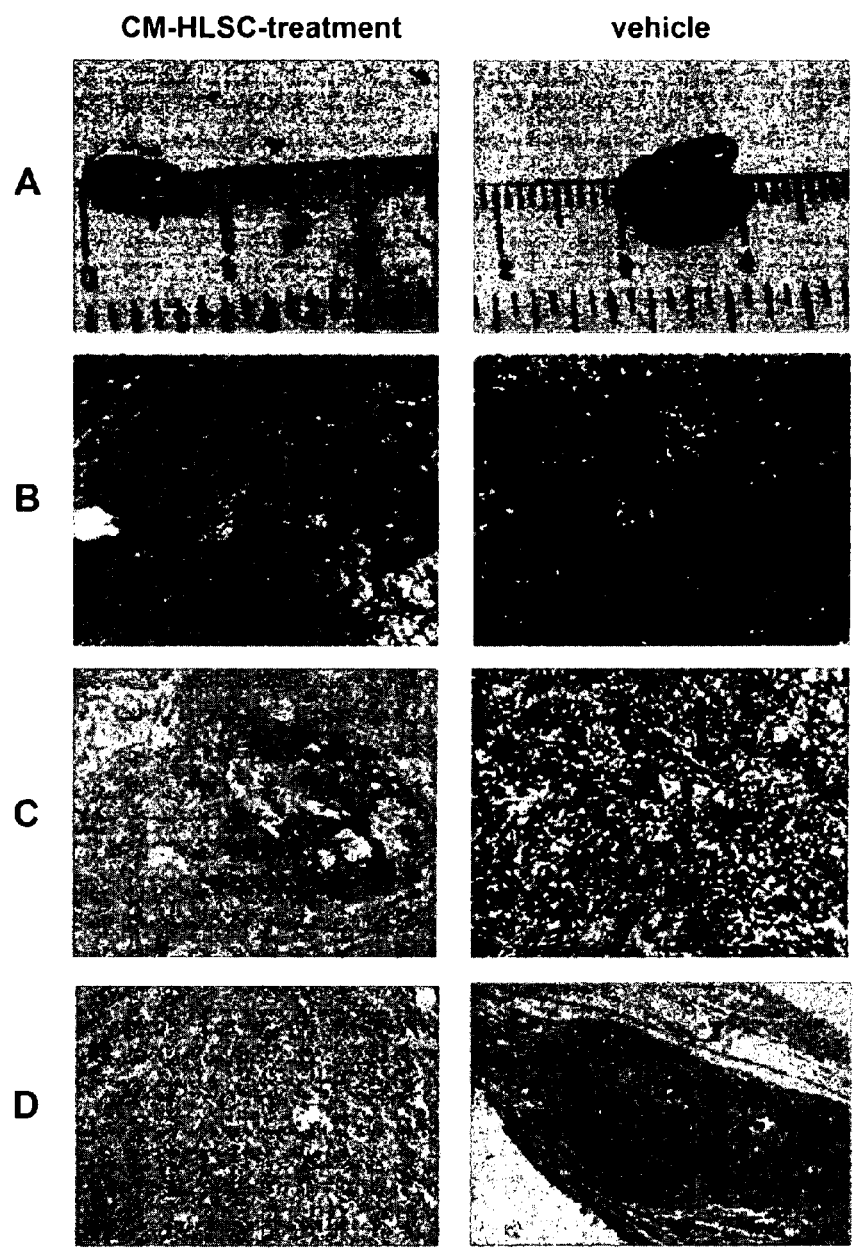

FIG. 9 are micrographs showing the in vivo inhibition of the tumour growth by HLSC-CM treatment and the induced intra-tumour apoptosis (A). Representative micrographs of recovered HepG2 tumors after 4 weeks, from CM-treated and not treated mice. B) Haematoxylin & Eosin and PCNA staining (C) of HepG2 tumors CM-treated or not treated. D) Representative micrographs showing apoptosis of recovered HepG2 tumors treated with vehicle alone or HepG2 tumors treated with CM from HLSC.

EXPERIMENTAL SECTION

Materials and Methods

Cell Culture

A human hepatoma cell line, HepG2, was cultured in DMEM supplemented with 10% fetal bovine serum, 100 μg/ml penicillin and 100 μg/ml streptomycin and maintained in an incubator with a humidified atmosphere of 5% $CO_2$ at 37° C.

Human liver stem cells (HLSCs) were cultured in α-MEM/EBM (3:1), supplemented with 10% fetal bovine serum, 100 μg/ml penicillin and 100 μg/ml streptomycin. EBM was reconstituted with hEGF (human Epithelial Growth Factor), Hydrocortisone, GA (gentamicin), BBE (Brain Bovine Extract).

MCF-7 breast adenocarcinoma cell lines were obtained from American Type Culture Collection (Manassas, Va.) and were cultured in DMEM supplemented with 10% of FCS, 100 μg/ml penicillin and 100 μg/ml streptomycin and maintained in an incubator with a humidified atmosphere of 5% $CO_2$ at 37° C.

A primary culture of Kaposi's sarcoma cells (KS cells) was obtained from a cutaneous lesion of a patient bearing renal allograft under immunosuppressive therapy and was cultured in RPMI 1640 medium supplemented with 10% of FCS, 100 μg/ml penicillin and 100 μg/ml streptomycin.

Purification of Conditioned Medium (CM) from HLSC Cells

The cell free conditioned medium (CM) from HLSCs was prepared by collecting the cell culture medium by centrifugation after 24 hours of culture. The experiments were performed with a cell mass of $2 \times 10^6$ cells. The medium was ultracentrifuged and concentrated, at approximately 25 fold, by centrifugation at 2700 g for 75 minutes, with ultrafiltration units (Amicon Ultra-PL 3) having a 3 kDa molecular weight cut-off. A total volume of 250 μl of concentrated conditioned medium was obtained. The protein concentration of the concentrated CM used for the in vitro experiments was CM=4.8 mg/ml. In selected experiments, the cell free CM was treated with 1 U/ml RNase for 1 hour at 37° C. The reaction was stopped by the addition of 10 U/ml of RNase inhibitor.

CM composition Analysis by Raybio Biotin Label-Based Antibody Array

The expression levels of 507 human target proteins derived from HLSC-CM were simultaneously detected. CM was collected after 48 hours culture of $1 \times 10^6$ cells in the presence of αMEM supplemented with 0.2% of FCS as described in protein array protocol. The panel of molecules included cytokines, chemokines, adipokine, growth factors, angiogenic factors, proteases, soluble receptors, soluble adhesion molecules, and other proteins in cell culture supernatant.

To prepare HLSC-CM, cells were plated in 100 mm tissue culture dishes at a density of $1 \times 10^6$ cells per dish. Cells were then culture with complete culture medium for 24-48 hours. After that, medium was replaced with lower serum (0.2% FCS) and then the cells were cultured for 48 hours again once more. The CM was collected, and centrifuged at 1000 g. The CM was dialyzed before biotin-labeling step. Through a simple process, the primary amine of the proteins in the samples were biotinylated, followed by dialysis to remove free biotin. From here, the newly biotinylated samples were added onto the array membrane and incubated at room temperature. After incubation with HRP-streptavidin, the signals were visualized by chemiluminescence. In this array, an internal control to monitoring the whole process including biotin-label and antibody array was used. Results were analyzed with RayBio Analysis Tool which is a program specifically designed for analysis of RayBio Biotin Label-based Antibody Array. Further details on this assay may be found in the RayBio® Biotin Label-based Human Antibody Array I User Manual.

The complete results of the RayBio Biotin Label-based Antibody Array assay are summarised in the table herein below.

| Proteins | HLSC (densitometric analysis) | HLSC/MSC ratio |
| --- | --- | --- |
| 6Ckine | 6.11 | 2.06 |
| Activin A | 6.54 | 2.16 |
| Activin B | 5.42 | 2.18 |
| Activin C | 7.27 | 2.56 |
| Activin RIA/ALK-2 | 5.63 | 2.18 |
| Activin RIB/ALK-4 | 5.27 | 1.95 |
| Activin RII A/B | 5.18 | 1.76 |
| Activin RIIA | 5.28 | 1.71 |
| Adiponectin/Acrp30 | 5.57 | 1.48 |
| AgRP | 5.67 | 1.59 |
| ALCAM | 10.30 | 2.62 |
| Angiogenin | 9.40 | 2.38 |
| Angiopoietin-1 | 6.45 | 1.45 |
| Angiopoietin-2 | 5.92 | 1.48 |
| Angiopoietin-4 | 5.62 | 1.40 |
| Angiopoietin-like 1 | 5.76 | 1.36 |
| Angiopoietin-like 2 | 6.51 | 1.51 |
| Angiopoietin-like Factor | 6.26 | 1.53 |
| Angiostatin | 6.90 | 1.66 |
| APJ | 6.00 | 1.40 |
| AR (Amphiregulin) | 6.34 | 1.47 |
| APRIL | 7.03 | 1.47 |
| Artemin | 7.30 | 1.52 |
| Axl | 8.83 | 1.70 |
| B7-1/CD80 | 9.33 | 1.66 |
| BAFF R/TNFRSF13C | 9.12 | 1.48 |
| BCMA/TNFRSF17 | 4.68 | 1.79 |
| BD-1 | 4.64 | 1.77 |
| BDNF | 4.71 | 1.68 |
| beta-Catenin | 4.23 | 1.61 |
| beta-Defensin 2 | 4.31 | 1.63 |
| beta-NGF | 4.38 | 1.66 |
| BIK | 4.56 | 1.73 |
| BLC/BCA-1/CXCL13 | 4.36 | 1.56 |
| BMP-2 | 4.25 | 1.50 |
| BMP-3 | 4.43 | 1.43 |
| BMP-3b/GDF-10 | 4.34 | 1.43 |
| BMP-4 | 4.60 | 1.41 |
| BMP-5 | 4.46 | 1.40 |
| BMP-6 | 4.47 | 1.34 |
| BMP-7 | 4.44 | 1.31 |
| BMP-8 | 4.87 | 1.31 |
| BMP-15 | 4.74 | 1.33 |
| BMPR-IA/ALK-3 | 5.30 | 1.49 |
| BMPR-IB/ALK-6 | 6.35 | 1.69 |
| BMPR-II | 5.76 | 1.59 |
| BTC | 5.71 | 1.61 |
| Cardiotrophin-1/CT-1 | 5.89 | 1.61 |
| CCL14/HCC-1/HCC-3 | 5.92 | 1.50 |
| CCL28/VIC | 6.67 | 1.57 |
| CCR1 | 7.76 | 1.42 |
| CCR2 | 9.00 | 1.63 |
| CCR3 | 8.21 | 1.49 |
| CCR4 | 8.04 | 3.02 |
| CCR5 | 5.02 | 1.97 |
| CCR6 | 5.59 | 2.08 |
| CCR7 | 5.52 | 1.89 |
| CCR8 | 4.43 | 1.51 |
| CCR9 | 4.10 | 1.48 |
| CD14 | 4.21 | 1.55 |
| CD27/TNFRSF7 | 3.94 | 1.50 |
| CD30/TNFRSF8 | 3.70 | 1.38 |

-continued

| Proteins | HLSC (densitometric analysis) | HLSC/MSC ratio |
|---|---|---|
| CD30 Ligand/TNFSF8 | 4.28 | 1.40 |
| CD40/TNFRSF5 | 4.40 | 1.56 |
| CD40 Ligand/TNFSF5/CD154 | 4.14 | 1.38 |
| CD 163 | 3.69 | 1.33 |
| Cerberus 1 | 3.86 | 1.29 |
| Chem R23 | 3.59 | 1.22 |
| Chordin-Like 1 | 3.62 | 1.14 |
| Chordin-Like 2 | 3.74 | 1.16 |
| Csk | 5.97 | 1.51 |
| CLC | 4.23 | 1.20 |
| CNTF | 4.73 | 1.35 |
| CNTF R alpha | 4.51 | 1.29 |
| Coagulation Factor III/Tissue Factor | 4.70 | 1.38 |
| CRIM 1 | 8.98 | 2.55 |
| Cripto-1 | 5.26 | 1.50 |
| CRTH-2 | 5.11 | 1.44 |
| Cryptic | 5.65 | 1.59 |
| CTACK/CCL27 | 6.33 | 1.66 |
| CTGF/CCN2 | 6.97 | 1.77 |
| CTLA-4/CD152 | 10.38 | 2.31 |
| CV-2/Crossveinless-2 | 7.80 | 1.61 |
| CXCL14/BRAK | 6.49 | 2.03 |
| CXCL16 | 4.64 | 1.67 |
| CXCR1/IL-8 RA | 4.56 | 1.61 |
| CXCR2/IL-8 RB | 4.41 | 1.55 |
| CXCR3 | 4.01 | 1.56 |
| CXCR4 (fusin) | 3.85 | 1.44 |
| CXCR5/BLR-1 | 3.84 | 1.41 |
| CXCR6 | 3.92 | 1.40 |
| D6 | 3.77 | 1.38 |
| DAN | 4.02 | 1.36 |
| DANCE | 3.78 | 1.38 |
| DcR3/TNFRSF6B | 3.62 | 1.28 |
| Decorin | 9.12 | 2.86 |
| Dkk-1 | 4.35 | 1.36 |
| Dkk-3 | 3.41 | 1.12 |
| Dkk-4 | 3.50 | 1.09 |
| DR3/TNFRSF25 | 3.53 | 1.11 |
| DR6/TNFRSF21 | 4.20 | 1.25 |
| Dtk | 9.06 | 2.17 |
| EDA-A2 | 237.46 | 2.94 |
| EDAR | 6.79 | 1.88 |
| EDG-1 | 4.43 | 1.25 |
| EGF | 4.63 | 1.30 |
| EGF R/ErbB1 | 4.69 | 1.31 |
| EG-VEGF/PK1 | 5.03 | 1.34 |
| EMAP-II | 6.15 | 1.75 |
| ENA-78 | 6.28 | 1.74 |
| Endocan | 8.34 | 2.14 |
| Endoglin/CD105 | 8.97 | 2.02 |
| Endostatin | 8.59 | 1.53 |
| EN-RAGE | 5.09 | 2.04 |
| Eotaxin/CCL11 | 4.52 | 1.77 |
| Eotaxin-2/MPIF-2 | 4.27 | 1.47 |
| Eotaxin-3/CCL26 | 4.24 | 1.52 |
| Epiregulin | 3.87 | 1.43 |
| ErbB2 | 3.90 | 1.43 |
| ErbB3 | 4.17 | 1.56 |
| ErbB4 | 3.82 | 1.34 |
| Erythropoietin | 4.16 | 1.26 |
| E-Selectin | 3.79 | 1.33 |
| Endothelin | 14.95 | 3.86 |
| FADD | 3.77 | 1.29 |
| FAM3B | 6.05 | 1.76 |
| Fas/TNFRSF6 | 3.73 | 1.21 |
| Fas Ligand | 3.61 | 1.11 |
| FGF Basic | 3.67 | 1.08 |
| FGF-BP | 3.78 | 1.16 |
| FGF R3 | 4.05 | 1.19 |
| FGF R4 | 4.72 | 1.29 |
| FGF R5 | 17.21 | 2.92 |
| FGF-4 | 4.68 | 1.30 |
| FGF-5 | 4.05 | 1.13 |
| FGF-6 | 4.27 | 1.16 |
| FGF-7/KGF | 4.93 | 1.22 |
| FGF-8 | 4.89 | 1.37 |
| FGF-9 | 5.40 | 1.49 |
| FGF-10/KGF-2 | 5.74 | 1.56 |
| FGF-11 | 6.19 | 1.66 |
| FGF-12 | 8.68 | 1.98 |
| FGF-13 1B | 7.74 | 1.60 |
| FGF-16 | 5.31 | 1.77 |
| FGF-17 | 3.91 | 1.37 |
| FGF-18 | 4.00 | 1.44 |
| FGF-19 | 3.88 | 1.37 |
| FGF-20 | 3.67 | 1.33 |
| FGF-21 | 3.88 | 1.42 |
| FGF-23 | 3.90 | 1.22 |
| FLRG | 3.84 | 1.34 |
| Flt-3 Ligand | 3.69 | 1.32 |
| Follistatin | 5.33 | 1.58 |
| Follistatin-like 1 | 5.81 | 1.15 |
| Fractalkine | 3.94 | 1.28 |
| Frizzled-1 | 3.88 | 1.23 |
| Frizzled-3 | 3.80 | 1.18 |
| Frizzled-4 | 3.78 | 1.21 |
| Frizzled-5 | 4.52 | 1.36 |
| Frizzled-6 | 5.46 | 1.62 |
| Frizzled-7 | 4.17 | 1.23 |
| Galectin-3 | 5.86 | 1.56 |
| GASP-1/WFIKKNRP | 5.03 | 1.44 |
| GASP-2/WFIKKN | 4.39 | 1.20 |
| GCP-2/CXCL6 | 4.69 | 1.26 |
| GCSF | 5.57 | 1.52 |
| G-CSF R/CD 114 | 4.68 | 1.26 |
| GDF1 | 5.00 | 1.28 |
| GDF3 | 6.38 | 1.77 |
| GDF5 | 6.55 | 1.74 |
| GDF8 | 6.08 | 1.58 |
| GDF9 | 10.31 | 2.25 |
| GDF11 | 8.84 | 1.70 |
| GDF-15 | 4.64 | 1.34 |
| GDNF | 3.87 | 1.27 |
| GFR alpha-1 | 3.67 | 1.25 |
| GFR alpha-2 | 3.92 | 1.21 |
| GFR alpha-3 | 4.09 | 1.39 |
| GFR alpha-4 | 4.01 | 1.45 |
| GITR/TNFRF18 | 3.80 | 1.33 |
| GITR Ligand/TNFSF18 | 4.04 | 1.44 |
| Glucagon | 3.89 | 1.31 |
| Glut1 | 3.61 | 1.23 |
| Glut2 | 3.73 | 1.22 |
| Glut3 | 3.87 | 1.25 |
| Glut5 | 4.00 | 1.29 |
| Glypican 3 | 34.34 | 2.73 |
| Glypican 5 | 5.27 | 1.48 |
| GM-CSF | 4.20 | 1.24 |
| GM-CSF R alpha | 4.37 | 1.28 |
| Granzyme A | 4.92 | 1.41 |
| GREMLIN | 8.49 | 2.19 |
| GRO | 21.75 | 3.69 |
| GRO-a | 4.90 | 1.32 |
| Growth Hormone (GH) | 5.17 | 1.34 |
| Growth Hormone R (GHR) | 5.42 | 1.36 |
| HB-EGF | 5.37 | 1.46 |
| HCC-4/CCL16 | 4.91 | 1.33 |
| HCR/CRAM-A/B | 5.09 | 1.39 |
| Hepassocin | 6.08 | 1.61 |
| Heregulin/NDF/GGF/Neuregulin | 6.08 | 1.45 |
| HGF | 15.29 | 3.38 |
| HGFR | 6.53 | 1.31 |
| HRG-alpha | 4.47 | 1.40 |
| HRG-beta 1 | 4.09 | 1.25 |
| HVEM/TNFRSF14 | 4.06 | 1.24 |
| I-309 | 3.67 | 1.25 |
| ICAM-1 | 3.49 | 1.25 |
| ICAM-2 | 3.28 | 1.16 |
| ICAM-3 (CD50) | 3.77 | 1.15 |
| ICAM-5 | 3.49 | 1.24 |
| IFN-alpha/beta R1 | 3.50 | 1.19 |

| Proteins | HLSC (densitometric analysis) | HLSC/MSC ratio |
|---|---|---|
| IFN-alpha/beta R2 | 3.52 | 1.18 |
| IFN-beta | 3.66 | 1.19 |
| IFN-gamma | 3.67 | 1.17 |
| IFN-gamma R1 | 3.89 | 1.22 |
| IGFBP-1 | 4.95 | 1.39 |
| IGFBP-2 | 13.69 | 2.11 |
| IGFBP-3 | 6.11 | 1.66 |
| IGFBP-4 | 5.90 | 1.64 |
| IGFBP-6 | 27.78 | 4.59 |
| IGFBP-rp1/IGFBP-7 | 333.01 | 2.75 |
| IGF-I | 13.74 | 3.15 |
| IGF-I SR | 5.23 | 1.35 |
| IGF-II | 4.76 | 1.26 |
| IGF-II R | 6.57 | 1.69 |
| IL-1 alpha | 9.12 | 2.26 |
| IL-1 beta | 4.87 | 1.30 |
| IL-1 F5/FIL1delta | 5.25 | 1.42 |
| IL-1 F6/FIL1 epsilon | 7.50 | 1.79 |
| IL-1 F7/FIL1 zeta | 5.73 | 1.37 |
| IL-1 F8/FIL1 eta | 5.91 | 1.25 |
| IL-1 F9/IL-1 H1 | 6.37 | 1.24 |
| IL-1 F10/IL-1HY2 | 4.26 | 1.19 |
| IL-1 R3/IL-1 R AcP | 4.11 | 1.25 |
| IL-1 R4/ST2 | 4.29 | 1.33 |
| IL-1 R6/IL-1 Rrp2 | 3.69 | 1.21 |
| IL-1 R8 | 3.32 | 1.13 |
| IL-1 R9 | 3.32 | 1.07 |
| IL-1 ra | 3.36 | 1.11 |
| IL-1 sRI | 3.29 | 1.09 |
| IL-1 sRII | 3.25 | 1.03 |
| IL-2 | 3.53 | 1.12 |
| IL-2 R alpha | 4.82 | 1.43 |
| IL-2 R beta/CD122 | 3.88 | 1.15 |
| IL-2 R gamma | 4.07 | 1.17 |
| IL-3 | 4.34 | 1.26 |
| IL-3 R alpha | 4.64 | 1.24 |
| IL-4 | 4.72 | 1.25 |
| IL-4 R | 5.53 | 1.11 |
| IL-5 | 6.31 | 1.60 |
| IL-5 R alpha | 16.15 | 2.21 |
| IL-6 | 35.23 | 1.46 |
| IL-6 R | 6.41 | 1.51 |
| IL-7 | 6.01 | 1.51 |
| IL-7 R alpha | 6.10 | 1.30 |
| IL-8 | 38.69 | 1.37 |
| IL-9 | 6.41 | 1.47 |
| IL-10 | 5.27 | 1.39 |
| IL-10 R alpha | 5.42 | 1.36 |
| IL-10 R beta | 5.54 | 1.38 |
| IL-11 | 5.71 | 1.20 |
| IL-12 p40 | 6.30 | 1.17 |
| IL-12 p70 | 4.14 | 1.22 |
| IL-12 R beta 1 | 3.44 | 1.08 |
| IL-12 R beta 2 | 8.52 | 1.70 |
| IL-13 | 3.81 | 1.11 |
| IL-13 R alpha 1 | 4.12 | 1.14 |
| IL-13 R alpha 2 | 3.59 | 1.03 |
| IL-15 | 4.07 | 1.19 |
| IL-15 R alpha | 4.37 | 1.19 |
| IL-16 | 4.16 | 1.17 |
| IL-17 | 4.13 | 1.18 |
| IL-17B | 4.59 | 1.17 |
| IL-17B R | 4.89 | 1.16 |
| IL-17C | 5.24 | 1.23 |
| IL-17D | 5.18 | 1.24 |
| IL-17E | 5.74 | 1.41 |
| IL-17F | 5.96 | 1.40 |
| IL-17R | 5.29 | 1.35 |
| IL-17RC | 9.68 | 2.10 |
| IL-17RD | 6.54 | 1.60 |
| IL-18 BPa | 7.23 | 1.50 |
| IL-18 R alpha/IL-1 R5 | 5.76 | 1.44 |
| IL-18 R beta/AcPL | 5.84 | 1.44 |
| IL-19 | 6.69 | 1.61 |
| IL-20 | 6.79 | 1.58 |
| IL-20 R alpha | 15.60 | 3.16 |
| IL-20 R beta | 7.48 | 1.34 |
| IL-21 | 3.14 | 0.98 |
| IL-21 R | 3.18 | 0.95 |
| IL-22 | 3.34 | 0.91 |
| IL-22 BP | 3.22 | 0.93 |
| IL-22 R | 3.51 | 0.97 |
| IL-23 | 4.14 | 1.07 |
| IL-23 R | 3.75 | 1.06 |
| IL-24 | 4.14 | 1.07 |
| IL-26 | 4.28 | 1.17 |
| IL-27 | 5.71 | 1.42 |
| IL-28A | 9.23 | 2.20 |
| IL-29 | 5.31 | 1.18 |
| IL-31 | 4.89 | 1.23 |
| IL-31 RA | 5.80 | 1.26 |
| Inhibin A | 5.19 | 1.31 |
| Inhibin B | 5.93 | 1.37 |
| Insulin | 5.29 | 1.25 |
| Insulin R | 5.13 | 1.22 |
| Insulysin/IDE | 7.60 | 1.78 |
| IP-10 | 5.86 | 1.36 |
| I-TAC/CXCL11 | 5.83 | 1.40 |
| Kininostatin/kininogen | 7.18 | 1.75 |
| Kremen-1 | 6.35 | 1.54 |
| Kremen-2 | 13.18 | 3.01 |
| Lck | 7.05 | 1.42 |
| Latent TGF-beta bp1 | 28.04 | 4.90 |
| LBP | 4.34 | 1.23 |
| LECT2 | 3.38 | 1.00 |
| Lefty-A | 3.38 | 1.01 |
| Leptin R | 3.66 | 0.98 |
| Leptin (OB) | 3.52 | 1.03 |
| LFA-1 alpha | 3.75 | 1.05 |
| LIF | 4.12 | 1.09 |
| LIF R alpha | 4.43 | 1.02 |
| LIGHT/TNFSF14 | 4.34 | 1.09 |
| Lipocalin-1 | 4.58 | 1.14 |
| LRP-1 | 9.89 | 1.81 |
| LRP-6 | 29.80 | 2.28 |
| L-Selectin (CD62L) | 5.94 | 1.51 |
| Luciferase | 5.29 | 1.25 |
| Lymphotactin/XCL1 | 8.21 | 1.50 |
| Lymphotoxin beta/TNFSF3 | 5.97 | 1.39 |
| Lymphotoxin beta R/TNFRSF3 | 5.61 | 1.30 |
| MAC-1 | 5.54 | 1.20 |
| MCP-1 | 22.87 | 1.84 |
| MCP-2 | 5.83 | 1.37 |
| MCP-3 | 6.96 | 1.65 |
| MCP-4/CCL13 | 6.09 | 1.48 |
| M-CSF | 6.90 | 1.65 |
| M-CSF R | 7.02 | 1.62 |
| MDC | 8.30 | 1.64 |
| MFG-E8 | 8.93 | 1.62 |
| MFRP | 3.43 | 0.98 |
| MIF | 3.73 | 1.02 |
| MIG | 3.67 | 1.03 |
| MIP-1a | 5.17 | 1.42 |
| MIP-1b | 3.49 | 0.98 |
| MIP-1d | 3.45 | 0.93 |
| MIP 2 | 11.45 | 2.56 |
| MIP-3 alpha | 4.64 | 1.33 |
| MIP-3 beta | 3.68 | 1.03 |
| MMP-1 | 5.06 | 1.20 |
| MMP-2 | 4.30 | 1.14 |
| MMP-3 | 4.08 | 0.75 |
| MMP-7 | 4.49 | 0.93 |
| MMP-8 | 4.80 | 1.15 |
| MMP-9 | 4.25 | 0.98 |
| MMP-10 | 6.05 | 1.44 |
| MMP-11/Stromelysin-3 | 5.23 | 1.22 |
| MMP-12 | 5.12 | 1.33 |
| MMP-13 | 5.75 | 1.40 |
| MMP-14 | 7.60 | 1.79 |
| MMP-15 | 5.71 | 1.39 |

| Proteins | HLSC (densitometric analysis) | HLSC/MSC ratio |
|---|---|---|
| MMP-16/MT3-MMP | 7.86 | 1.80 |
| MMP-19 | 9.10 | 1.70 |
| MMP-20 | 8.06 | 1.68 |
| MMP-24/MT5-MMP | 6.44 | 1.48 |
| MMP-25/MT6-MMP | 6.20 | 1.36 |
| Musk | 6.62 | 1.41 |
| MSP alpha Chain | 6.85 | 1.40 |
| MSP beta-chain | 16.76 | 2.65 |
| NAP-2 | 9.61 | 1.71 |
| NCAM-1/CD56 | 5.11 | 1.24 |
| Neuritin | 4.04 | 1.06 |
| NeuroD1 | 3.86 | 1.07 |
| Neuropilin-2 | 3.58 | 1.01 |
| Neurturin | 3.58 | 0.94 |
| NGF R | 3.63 | 1.03 |
| NOV/CCN3 | 3.58 | 1.13 |
| NRG1 Isoform GGF2 | 3.60 | 1.10 |
| NRG1-alpha/HRG1-alpha | 3.58 | 1.03 |
| NRG1-beta1/HRG1-beta1 | 4.12 | 1.20 |
| NRG2 | 4.09 | 1.02 |
| NRG3 | 4.45 | 1.11 |
| NT-3 | 3.73 | 0.96 |
| NT-4 | 4.10 | 0.85 |
| Orexin A | 4.34 | 0.65 |
| Orexin B | 4.60 | 0.55 |
| OSM | 4.89 | 0.69 |
| Osteoactivin/GPNMB | 5.20 | 0.98 |
| Osteocrin | 8.16 | 1.73 |
| Osteoprotegerin/TNFRSF11B | 265.56 | 5.65 |
| OX40 Ligand/TNFSF4 | 11.27 | 2.49 |
| PARC/CCL18 | 5.35 | 1.26 |
| PD-ECGF | 5.31 | 1.20 |
| PDGF R alpha | 5.73 | 1.32 |
| PDGF R beta | 6.80 | 1.49 |
| PDGF-AA | 7.08 | 1.54 |
| PDGF-AB | 6.91 | 1.52 |
| PDGF-BB | 7.03 | 1.51 |
| PDGF-C | 7.12 | 1.43 |
| PDGF-D | 7.08 | 1.31 |
| PECAM-1/CD31 | 4.21 | 1.18 |
| Pentraxin3/TSG-14 | 11.67 | 2.24 |
| Persephin | 4.49 | 1.20 |
| PF4/CXCL4 | 3.88 | 1.10 |
| PlGF | 3.69 | 1.10 |
| PLUNC | 3.72 | 1.17 |
| Pref-1 | 3.88 | 1.20 |
| Progranulin | 4.96 | 1.52 |
| Prolactin | 4.16 | 1.26 |
| P-selectin | 3.86 | 1.10 |
| RAGE | 3.93 | 1.06 |
| RANK/TNFRSF11A | 4.43 | 1.17 |
| RANTES | 3.86 | 1.05 |
| RELM beta | 3.74 | 0.98 |
| RELT/TNFRSF19L | 4.28 | 0.93 |
| ROBO4 | 4.21 | 1.08 |
| S100 A8/A9 | 4.84 | 1.18 |
| S100A10 | 4.89 | 1.19 |
| SAA | 5.14 | 1.23 |
| SCF | 7.37 | 1.53 |
| SCF R/CD117 | 5.51 | 1.32 |
| SDF-1/CXCL12 | 5.32 | 1.18 |
| sFRP-1 | 6.65 | 1.47 |
| sFRP-3 | 6.42 | 1.35 |
| sFRP-4 | 69.46 | 5.43 |
| sgp130 | 15.48 | 2.93 |
| SIGIRR | 7.82 | 1.55 |
| Siglec-5/CD170 | 7.13 | 1.47 |
| Siglec-9 | 7.91 | 1.63 |
| SLPI | 7.96 | 1.29 |
| Smad 1 | 4.78 | 1.23 |
| Smad 4 | 10.65 | 2.26 |
| Smad 5 | 4.59 | 1.15 |
| Smad 7 | 4.59 | 1.22 |
| Smad 8 | 3.92 | 1.09 |
| SMDF/NRG1Isoform | 4.11 | 1.05 |
| Soggy-1 | 3.92 | 1.14 |
| Sonic Hedgehog (Shh N-terminal) | 3.77 | 1.10 |
| SPARC | 56.56 | 3.63 |
| Spinesin | 6.40 | 1.68 |
| TACI/TNFRSF13B | 4.40 | 1.10 |
| Tarc | 3.85 | 1.07 |
| TCCR/WSX-1 | 3.80 | 1.00 |
| TECK/CCL25 | 3.79 | 0.98 |
| TFPI | 5.18 | 1.22 |
| TGF-alpha | 4.28 | 1.09 |
| TGF-beta 1 | 4.64 | 1.19 |
| TGF-beta 2 | 4.85 | 1.22 |
| TGF-beta 3 | 5.26 | 1.32 |
| TGF-beta 5 | 5.28 | 1.29 |
| TGF-beta RI/ALK-5 | 6.94 | 1.51 |
| TGF-beta RII | 5.43 | 1.30 |
| TGF-beta RIIb | 5.72 | 1.34 |
| TGF-beta RIII | 6.70 | 1.53 |
| Thrombopoietin (TPO) | 7.40 | 0.94 |
| Thrombospondin (TSP) | 325.53 | 3.99 |
| Thrombospondin-1 | 281.16 | 3.76 |
| Thrombospondin-2 | 10.81 | 1.94 |
| Thrombospondin-4 | 7.96 | 1.57 |
| Thymopoietin | 7.60 | 1.44 |
| Tie-1 | 4.03 | 0.88 |
| Tie-2 | 3.92 | 0.86 |
| TIMP-1 | 137.73 | 1.08 |
| TIMP-2 | 54.09 | 7.91 |
| TIMP-3 | 7.21 | 1.73 |
| TIMP-4 | 4.31 | 1.05 |
| TL1A/TNFSF15 | 4.70 | 1.14 |
| TLR1 | 4.81 | 1.21 |
| TLR2 | 5.77 | 1.36 |
| TLR3 | 4.47 | 1.06 |
| TLR4 | 4.16 | 1.01 |
| TMEFF1/Tomoregulin-1 | 4.91 | 1.10 |
| TMEFF2 | 4.66 | 1.16 |
| TNF-alpha | 5.07 | 1.26 |
| TNF-beta | 5.36 | 1.26 |
| TNF RI/TNFRSF1A | 8.08 | 1.77 |
| TNF RII/TNFRSF1B | 5.79 | 1.19 |
| TRADD | 5.70 | 1.26 |
| TRAIL/TNFSF10 | 5.83 | 1.26 |
| TRAIL R1/DR4/TNFRSF10A | 6.28 | 1.40 |
| TRAIL R2/DR5/TNFRSF10B | 6.57 | 1.36 |
| TRAIL R3/TNFRSF10C | 6.98 | 1.44 |
| TRAIL R4/TNFRSF10D | 8.02 | 1.38 |
| TRANCE | 9.17 | 1.53 |
| TREM-1 | 4.77 | 0.95 |
| TROY/TNFRSF19 | 5.21 | 1.04 |
| TSG-6 | 5.72 | 1.10 |
| TSLP | 4.90 | 1.03 |
| TWEAK/TNFSF12 | 5.00 | 1.03 |
| TWEAK R/TNFRSF12 | 5.14 | 1.07 |
| Ubiquitin + 1 | 4.92 | 1.03 |
| uPA | 4.94 | 0.90 |
| uPAR | 5.41 | 1.11 |
| Vasorin | 6.12 | 1.27 |
| VCAM-1 (CD106) | 5.02 | 1.11 |
| VE-Cadherin | 5.20 | 1.18 |
| VEGF | 10.00 | 1.61 |
| VEGF R2 (KDR) | 5.73 | 1.25 |
| VEGF R3 | 5.48 | 1.19 |
| VEGF-B | 5.24 | 1.15 |
| VEGF-C | 7.98 | 1.60 |
| VEGF-D | 6.11 | 1.18 |
| VEGI/TNFSF15 | 6.03 | 1.20 |
| WIF-1 | 6.07 | 1.21 |
| WISP-1/CCN4 | 6.68 | 1.30 |
| XEDAR | 7.81 | 1.46 |

HLSC-HepG2 Co-Culture Experiments

In order to investigate if HLSCs are capable of reversing the aggressive phenotype of cancer cells, the hepatocellular cell line HepG2 was co-cultured in transwell chambers with HLSC. At the end of the experiments, the proliferation of HepG2 was evaluated. The lower compartment was seeded with HepG2 ($2.5 \times 10^4$ cells). The upper compartment was seeded with HLSC ($1 \times 10^5$). The co-culture was maintained for 4 days. After 4 days, the medium was removed and the HepG2 were fixed in 10% formalin and stained with H&E.

Cell Proliferation

HepG2 were seeded at 8,000 cells/well in 96-well plates in DMEM (Sigma) deprived of FCS using different concentrations of CM. In order to investigate whether CM derived from HLSCs exerted its anti-tumor activity also on cell lines from different tumours, MCF-7 breast adenocarcinoma and Kaposi's sarcoma cells were used, and the anti-tumour effects were compared with those observed on HepG2. DNA synthesis was detected as incorporation of 5-bromo-2'-deoxy-uridine (BrdU) into the cellular DNA after 48 hours of culture. The cells were then fixed with 0.5 M ethanol/HCl and incubated with nuclease to digest the DNA. The BrdU incorporated into the DNA was detected with an anti-BrdU peroxidase-conjugated monoclonal antibody (mAb) and visualized with a soluble chromogenic substrate. The optical density was measured with an ELISA reader at 405 nm.

Apoptosis Assay

HepG2, MCF-7 and KS cells were seeded at 8,000 cells/well in 96-well plates in low glucose DMEM (Sigma) with 10% FCS and in the presence of Doxorubicin (100 ng/ml, Sigma) or vincristine (50 ng/ml, Sigma) or different concentrations of CM (0.5; 1; 2; 8; 16% of 25× concentrated CM). Apoptosis was evaluated with the TUNEL assay (ApopTag Oncor, Gaithersburg, Md., USA).

In Vivo Experimental Design

Male 4- to 5-weeks-old SCID mice were purchased from Charles River Laboratories. All mice were housed in a clean facility and maintained for 1 week to acclimatize. On day 0, two injections of $3 \times 10^6$ HepG2 tumor cells resuspended in serum-free DMEM with Matrigel basement membrane matrix at a 1:1 ratio were administered. HepG2 were injected in a total volume of 0.2 ml into the left and right inguinal area of SCID mice. Mice were randomized into two treatment groups: the test group, which received 20 µl of 25× concentrated CM intra-tumour (i.t.) injections (n=3), and the control group, which was injected with 20 µl of PBS (n=3). Tumors became palpable as of day 10. CM treatment started 10 days after tumor transplantation with three subsequent i.t. injections. A total of 3 injections of 20 µl CM were administered to each developed tumor. Treatment started when tumors reached the volume of approximately 15 mm$^3$. The animals were monitored for activity and physical condition everyday, and the determination of body weight and measurement of tumor volume were effected at each treatment.

Tumours were measured with calipers. The tumour volume was determined measuring two perpendicular diameters of the implanted tumours and was calculated using the formula ½a×b$^2$ wherein a is the long diameter and b is the short diameter.

Morphological Studies

Tumours were fixed in 10% buffered neutral formalin, routinely processed, embedded in paraffin, sectioned at 5 µm, and stained with H&E for microscopic examination. Immunohistochemistry for detection of proliferation was performed using the anti-PCNA monoclonal antibody. Sections were blocked and labeled with anti-mouse HRP secondary antibody (1:300 dilution). Omission of the primary antibodies or substitution with non immune mouse IgG was used as the control. Apoptosis was evaluated in paraffin-embedded tumour sections by TUNEL. Ten non consecutive sections were counted for apoptotic-positive tumour cells at 630× magnification. Hoechst 33258 dye was added for nuclear staining.

Statistical Analysis

All data of different experimental procedures are expressed as the average+SD. Statistical analysis was performed by ANOVA with Newmann-Keuls multi-comparison test where appropriated.

Results

In Vitro Biological Effect of HLSC-CM on Tumour Cells

CM Derived from HLSC Inhibits In Vitro Proliferation of HepG2 Cells

The anti-tumour activity of CM, derived from human HLSC, was assessed in vitro by measuring their ability to inhibit proliferation of the HepG2 cell line.

Figure 1:
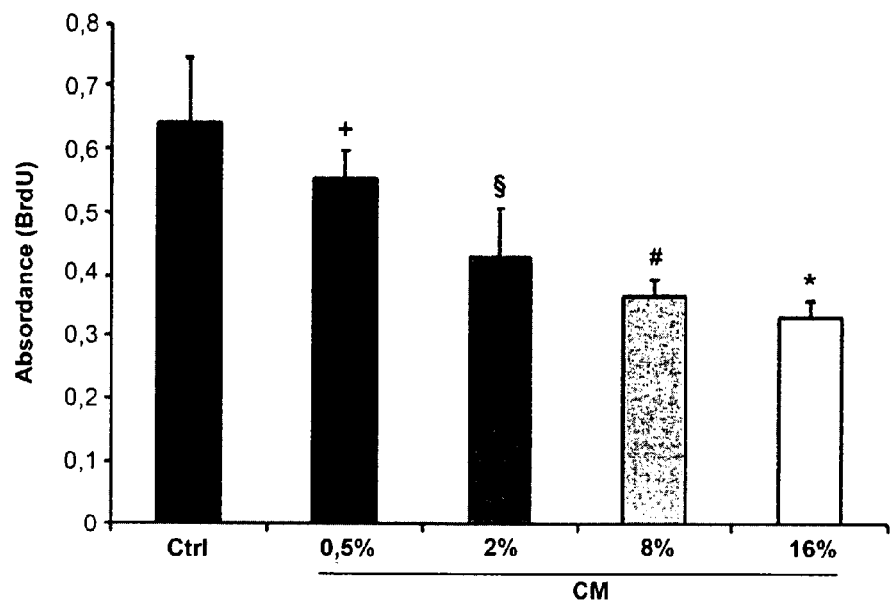
Figure 2:
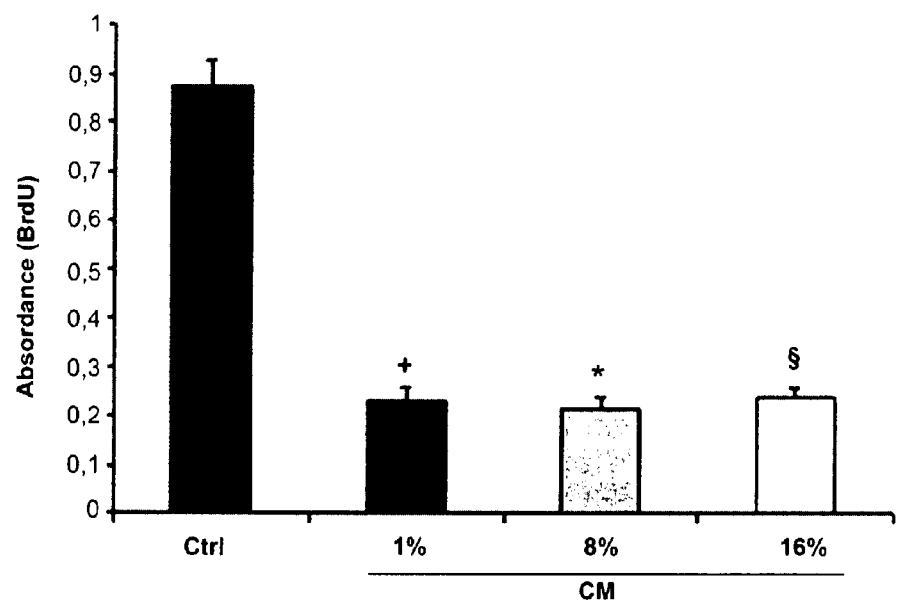

Incubation of HepG2 with different doses of CM for 48 hours (FIG. 1) and 4 days (FIG. 2), significantly inhibits proliferation compared to control cells incubated with vehicle alone.

CM Derived from HLSC Inhibits In Vitro Proliferation of MCF-7 and Ks Cells

Figure 3:
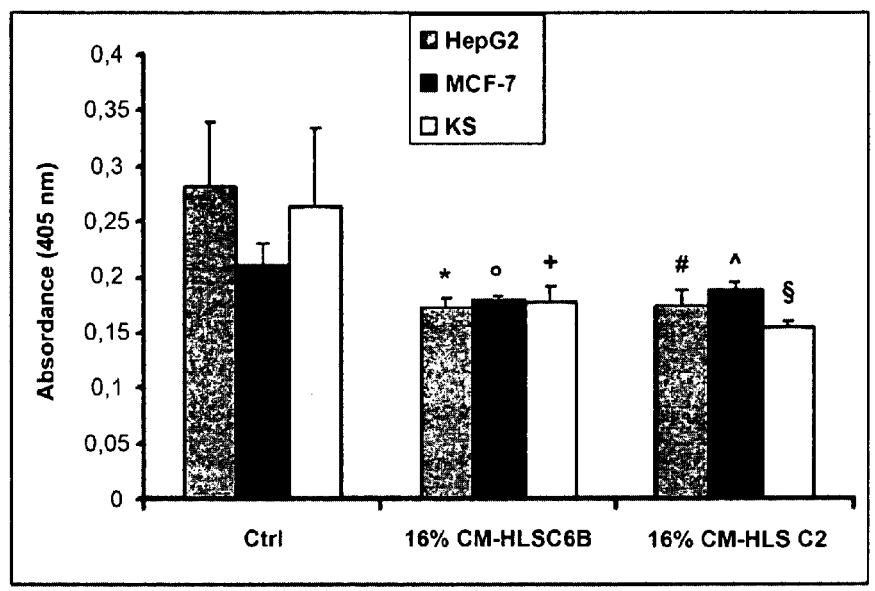

In order to investigate whether the anti-tumour effects of tissue resident stem cells were specific against tumours originated from the same tissue, the effect of HLSC-CM on cancer cells from tumours of unrelated organs, such as breast adenocarcinoma and Kaposi's sarcoma, was evaluated. Incubation for 48 hours of MCF-7 breast adenocarcinoma and of Kaposi's sarcoma cells with 16% of CM (FIG. 3) derived from two different preparations of HLSC(HLSC-6B and HLSC-2) significantly inhibit proliferation compared to control cells incubated with vehicle alone.

CM Derived from HLSC Induced In Vitro Apoptosis of HepG2 Cells

Figure 4:
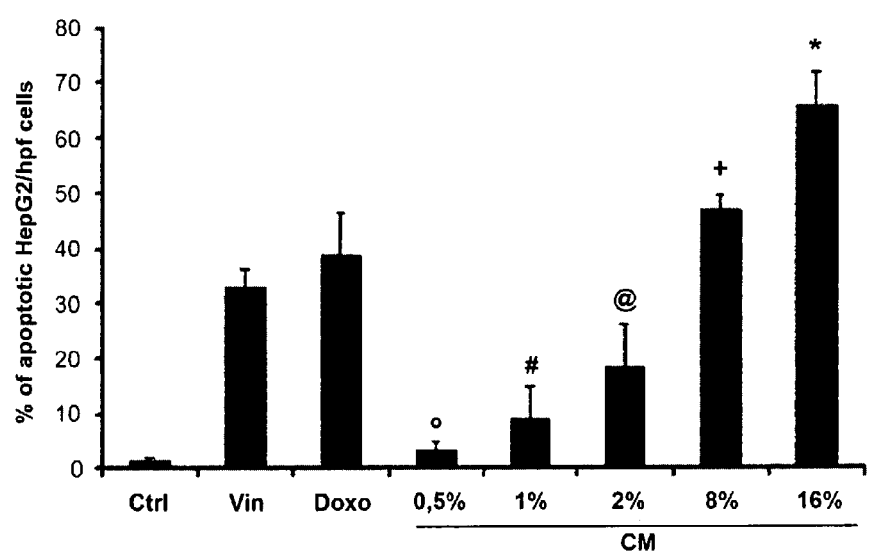

Incubation of HepG2 with HLSC-CM for 24 hours, significantly promoted apoptosis compared to control incubated with vehicle alone and compared to doxorubicin or vincristine stimulation (apoptotic molecules; considered positive controls) (FIG. 4).

CM derived from HLSC Promoted In Vitro Apoptosis of MCF-7 and KS Cells

Figure 5:
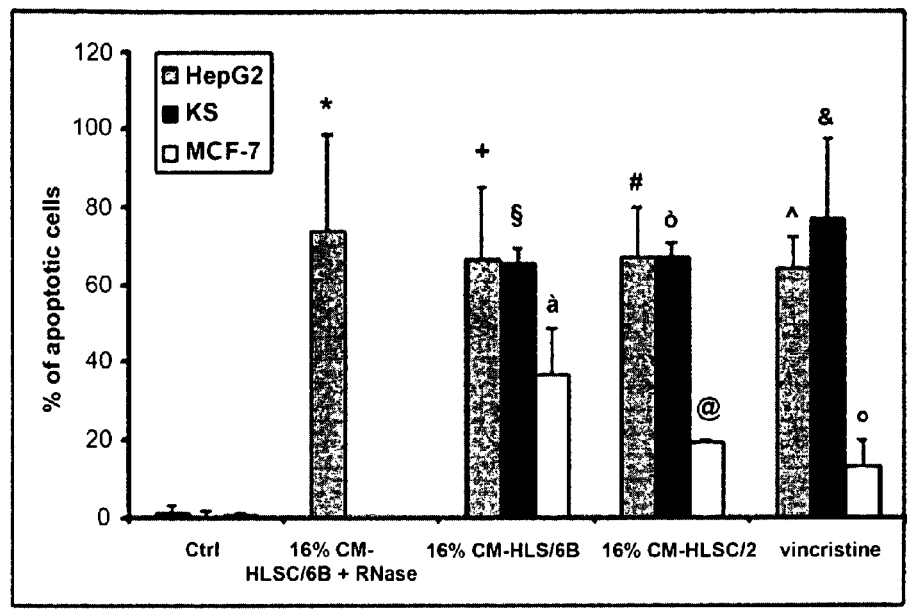

Incubation of MCF-7 breast adenocarcinoma and of Kaposi's sarcoma cells for 48 hours with 16% of CM (FIG. 5) derived from HLSC-6B significantly induced apoptosis, compared to control cells incubated with vehicle alone, with effects which are similar to those of vincristine, a chemotherapeutic drug.

In Vivo Biological Effect of Cm on HepG2 Tumor Growth Results

Figure 6:
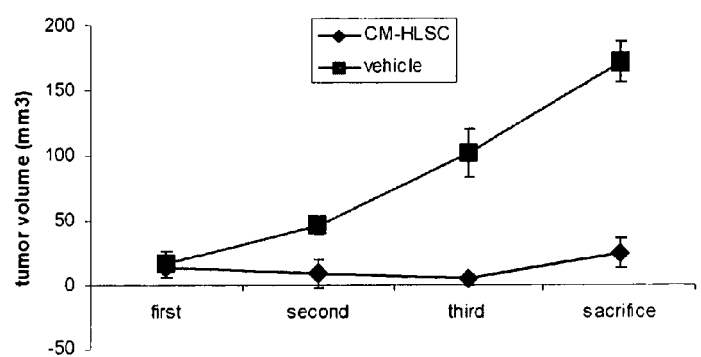
FIG. 6 is a graph showing the anti-tumour activity of HLSC-CM administrated i.t. into SCID mice transplanted with HepG2. Tumour volume was determined by measuring with a caliper two perpendicular diameters of the implant every week.
Figure 7:
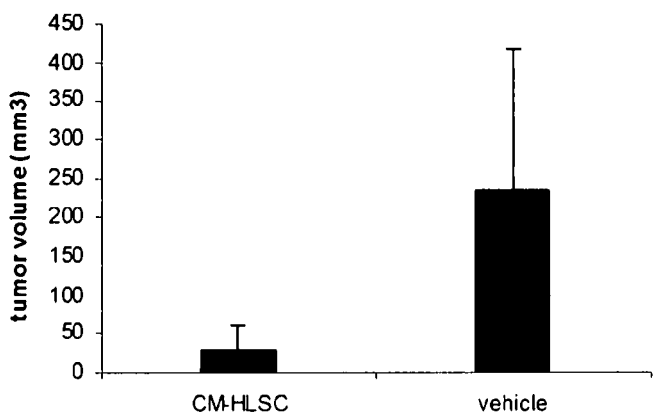
FIG. 7 is a graph showing the data obtained by measuring the tumour volume of recovered HepG2 tumors after CM-HLSC (n=6) or vehicle (n=6) i.t. treatment at time of mice sacrifice. Tumor volume was determined by measuring with a caliper two perpendicular diameters of the implant every week.
Figure 8:
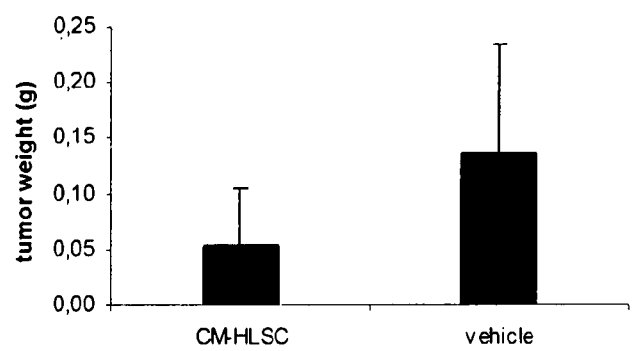
FIG. 8 is a graph showing the data obtained by measuring the tumour weight of recovered HepG2 tumors after CM-HLSC (n=6) or vehicle (n=6) i.t. treatment at time of mice sacrifice.

Tumor Growth and Proliferation were Inhibited by CM Derived Form HLSC in Hepatoma Xenograft Model in SCID Mice To determine the effect of CM derived from HLSC on tumor growth in vivo, SCID mice were subcutaneously transplanted with the human hepatocarcinoma cell line HepG2. Ten days after the injection of HepG2, when the volume of tumors was about 15 mm$^3$, mice were treated with intra-tumor injection of CM, for a maximum of 20 µl of volume. In control mice, tumours were injected with 20 µl of PBS. After ten days of HepG2 injection, all tumors were recovered and analyzed. In this xenograft model, intra-tumor injection of CM (FIG. 6; FIG. 9, Panel A) showed a inhibition effect on tumor growth. In addition, Histological analysis showed areas of necrosis in tumors treated with CM (FIG. 9, Panel B) and anti-proliferative effect was observed using PCNA staining (FIG. 9, Panel C). To determine the effect of CM in intra-tumor apoptosis, paraffin sections from tumors treated with CM were analyzed by TUNEL. CM treatments induced apoptosis FIG. 9, Panel B, compared to tumours treated with vehicle alone (FIG. 9, Panel D). At the moment of sacrifice, the tumour volume (FIG. 7) and tumour weight (FIG. 8) were measured.

The Wnt/β-catenin signalling pathway is known to be implicated in embryogenesis and carcinogenesis. Clinical studies have reported that abnormal activation of Wnt/β-catenin pathway is frequently involved in hepatocarcinogenesis. The Wnt-1 ligand has been reported to be abnormally expressed in a variety of human cancers including HCC.

Without being bound to any theory, the present inventors hypothesize that one of the mechanisms possibly underlying the anti-tumour effects of the stem cell-derived conditioned media tested by the inventors are reported above, might be the inhibition of the Wnt/β-catenin signalling pathway.

COMPARATIVE EXAMPLE

Materials and Methods

HepG2 was cultured in DMEM supplemented with 10% foetal bovine serum, 100 μg/ml penicillin and 100 μg/ml streptomycin and maintained in an incubator with a humidified atmosphere of 5% $CO_2$ at 37° C.

HLSC were cultured in α-MEM/EBM (3:1), supplemented with 10% foetal bovine serum. The day before HLSC CM collection, HLSC were incubated with only α-MEM supplemented with 10% foetal bovine serum in order to eliminate growth factors contained in EBM medium. This medium change was performed before each experiment that was done.
Apoptosis Assay HepG2 were seeded at 8,000 cell/well in 96-well plates in low glucose DMEM (Sigma) with 10% FCS and in the presence of 16% of 25× concentrated CM obtained from HLSC or MSC, or in the presence of 3 ng/ml of TGF-β. Apoptosis was evaluated with the TUNEL assay after 24 hours.

Statistical analysis was performed by ANOVA with Newmann-Keuls multi-comparison test.
Results Incubation of HepG2 with HLSC-CM for 24 hours, significantly promoted apoptosis compared to control incubated with vehicle alone. MSC-CM also promoted apoptosis of HepG2 as well TGF-β, but significantly less in respect to HLSC-CM.

Figure 10:
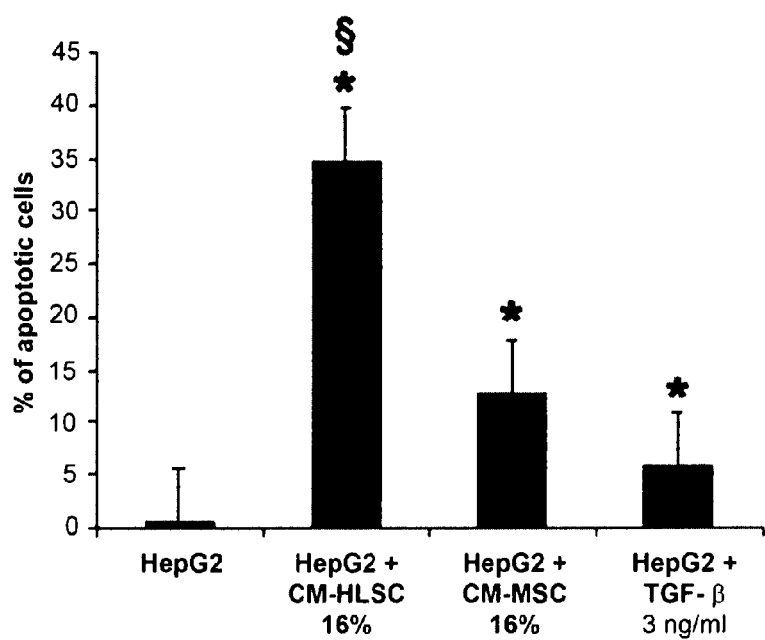

The results obtained are shown in FIG. 10.

FIG. 10 is a graph showing the results of in vitro apoptosis assay carried out by incubating HepG2 with 25× concentrated HLSC-CM (16%), or MSC-CM (16%), or with TGF-β (3 ng/ml) after 24 hours. Apoptosis of HepG2 was evaluated as the percentage of apoptotic cells. The results are expressed as mean±SD of an experiment performed in duplicate. * HepG2 treated with HLSC-CM (16%), or MSC-CM (16%), or with TGF-β (3 ng/ml) vs HepG2 not treated, $p<0.05$; §HepG2 treated with HLSC-CM (16%) vs HepG2 treated with MSC-CM (16%), or with TGF-β (3 ng/ml), $p<0.005$.

The invention claimed is:

1. A method for therapeutic treatment of a tumour disease comprising the steps of:
   providing a conditioned medium which includes a plurality of cell-secreted proteins and which is obtainable by culturing in a liquid cell culture medium an adult non-oval liver stem cell capable of differentiating into a plurality of differentiated cell types; and
   using the conditioned medium for the therapeutic treatment of a tumour disease.

2. The method according to claim 1, which includes providing a cell fraction containing the adult stem cell from which the conditioned medium is obtained.

3. The method according to claim 1, wherein the step of providing a conditioned medium includes providing a conditioned medium that is cell free.

4. The method according to claim 3, wherein the step of providing a conditioned medium includes obtaining the conditioned medium by a method including the steps of: (i) culturing an adult stem cell capable of differentiating into a plurality of differentiated cell types in a liquid cell culture medium for a predetermined period of time; and (ii) removing the cell fraction from the liquid cell culture medium, thereby obtaining a cell free conditioned medium which includes a plurality of cell-secreted proteins.

5. The method according to claim 4, wherein the step of removing the cell fraction from the liquid cell culture medium is performed by centrifugation or filtration.

6. The method according to claim 5, further comprising the step of subjecting the liquid cell culture medium to ultracentrifugation at a g-force of between about 20,000 and about 300,000 g.

7. The method according to claim 4, wherein the method of obtaining the conditioned medium further comprises the step of: (iii) removing from the cell free conditioned medium the fraction of matter having a nominal molecular weight lower than 3 kDa.

8. The method according to claim 7, wherein the step of removing includes removing the fraction of matter having a nominal molecular weight lower than 3 kDa from the cell free conditioned medium by ultrafiltration.

9. The method according to claim 7, wherein the method further comprises the step of treating the cell free conditioned medium obtained in step (ii) or in step (iii) with RNase.

10. The method according to claim 1, wherein the non-oval liver stem cell is capable of differentiating into a mature liver cell, an insulin-producing cell, an osteogenic cell and an epithelial cell.

11. The method according to claim 1, wherein the adult non-oval liver stem cell capable of differentiating into a plurality of differentiated cell types is a human cell.

12. The method according to claim 1, wherein the step of therapeutic treatment includes therapeutically treating a tumour disease selected from the group consisting of liver tumour, epithelial tumour, breast tumour, lung tumour, prostate tumour, gastric tumour, and colon tumour.

13. The method according to claim 1, wherein the step of therapeutic treatment includes therapeutically treating a tumour disease selected from the group consisting of hepatoma, Kaposi's sarcoma and breast adenocarcinoma.

14. A method including the step of using a medicament, wherein the medicament is
   a) a conditioned medium which includes a plurality of cell-secreted proteins and which is obtainable by culturing in a liquid cell culture medium an adult non-oval liver stem cell capable of differentiating into a plurality of differentiated cell types or
   b) the adult non-oval liver stem cell,
for the therapeutic treatment of a tumour disease.

15. The method according to claim 14, wherein the medicament is used for local or systemic administration.

16. The method according to claim 15, wherein the medicament is administrated by injection.

17. The method according to claim 6, wherein the liquid cell culture medium is subjected to ultracentrifugation at a g-force between about 80,000 and 200,000 g.

* * * * *